(12) United States Patent
Trammell, III

(10) Patent No.: US 7,705,731 B2
(45) Date of Patent: Apr. 27, 2010

(54) VERIFICATION AND SCREENING SYSTEM

(75) Inventor: Hoke S. Trammell, III, Omaha, NE (US)

(73) Assignee: Morpho Detection, Inc., Newark, CA (US)

( * ) Notice: Subject to any disclaimer, the term of this patent is extended or adjusted under 35 U.S.C. 154(b) by 219 days.

(21) Appl. No.: 11/385,936

(22) Filed: Mar. 20, 2006

(65) Prior Publication Data

US 2007/0222620 A1    Sep. 27, 2007

Related U.S. Application Data

(60) Provisional application No. 60/781,057, filed on Mar. 10, 2006.

(51) Int. Cl.
*G08B 13/14* (2006.01)

(52) U.S. Cl. .................. 340/568.1; 340/521; 340/522; 340/540; 340/541; 340/5.1; 340/5.3; 340/5.32; 340/573.1; 340/573.4

(58) Field of Classification Search .............. 340/568.1, 340/521, 522, 540, 5.12, 5.3, 5.32, 573.1, 340/573.4, 541
See application file for complete search history.

(56) References Cited

U.S. PATENT DOCUMENTS

| | | | |
|---|---|---|---|
| 3,758,849 A | 9/1973 | Susman et al. | |
| 4,137,567 A * | 1/1979 | Grube | ........................ 702/175 |
| 5,600,941 A | 2/1997 | Strosser | |
| 6,003,009 A | 12/1999 | Nishimura | |
| 6,044,353 A | 3/2000 | Pugliese, III | |
| 6,119,096 A | 9/2000 | Mann et al. | |
| 6,137,895 A | 10/2000 | Al-Sheikh | |
| 6,158,658 A | 12/2000 | Barclay | |
| 6,335,688 B1 | 1/2002 | Sweatte | |
| 6,362,739 B1 | 3/2002 | Burton | |
| 6,914,668 B2 * | 7/2005 | Brestel et al. | .................. 356/72 |
| 6,970,087 B2 | 11/2005 | Stis | |
| 7,136,513 B2 | 11/2006 | Waehner et al. | |
| 7,317,390 B2 | 1/2008 | Huey et al. | |
| 2004/0117638 A1 * | 6/2004 | Monroe | ...................... 713/186 |
| 2004/0190757 A1 | 9/2004 | Murphy et al. | |
| 2005/0024199 A1 * | 2/2005 | Huey et al. | .................. 340/521 |
| 2005/0057354 A1 * | 3/2005 | Jenkins et al. | .............. 340/522 |
| 2005/0256724 A1 * | 11/2005 | Rasin et al. | .................... 705/1 |
| 2006/0087439 A1 * | 4/2006 | Tolliver | ................... 340/573.1 |

FOREIGN PATENT DOCUMENTS

WO    2007089775 A2    8/2007

OTHER PUBLICATIONS

International Search Report of PCT/US2007/064297 Apr. 8, 2008 (6 Pages).

* cited by examiner

*Primary Examiner*—Tai T Nguyen
(74) *Attorney, Agent, or Firm*—Armstrong Teasdale LLP

(57) ABSTRACT

An inspection system including a first subsystem including a first identity verification system and a passenger screening system each configured to receive information from a passenger and store the verified information in a database, and a second subsystem including at least a second identity verification system configured to receive information from the passenger, the second subsystem configured to compare the verified identity information to the information received from the passenger at the second subsystem to verify the identity of the passenger.

25 Claims, 3 Drawing Sheets

VERIFICATION AND SCREENING SYSTEM

CROSS REFERENCE TO RELATED APPLICATIONS

This application claims the benefit of U.S. provisional application No. 60/781,057, filed on Mar. 10, 2006, which is herein incorporated by reference in its entirety.

BACKGROUND OF THE INVENTION

This invention relates generally to personnel screening systems, and more particularly to, an integrated passenger identity verification and screening kiosk.

The Transportation Security Administration (TSA) has recently mandated more stringent inspection procedures to be implemented by the travel industry to reduce the possibility of passengers boarding a carrier such as a plane, for example, carrying concealed weapons, explosives, or other contraband. To facilitate preventing passengers boarding a plane carrying concealed weapons, explosives, etc., the TSA requires that all passengers be screened prior to boarding the aircraft.

For example, passengers arriving at the airport terminal first submit to a manual verification process that generally includes presenting their boarding pass and a form of identification such as a driver's license or passport, for example, to security personnel. The security personnel then manually verify that the passenger has a valid boarding pass, the name on the identification corresponds to the name on the boarding pass, and that the picture on the license or passport corresponds to the passenger presenting the license and boarding pass to the security personnel.

After the manual verification process is completed, the passenger is requested to walk through a metal detector to ensure that the passenger is not carrying any concealed weapons. While the metal detector is reasonably effective at detecting specific quantities of metal, the metal detector can not distinguish between a possible weapon or other non-threatening items such as shoes that may include metallic portions. As a result, security personnel frequently request that passengers remove their shoes and place their shoes into the baggage screening system such that security personnel can visually verify the metallic object prior to the passenger boarding the plane and to also ascertain whether the shoes may conceal any explosive material or devices. Passengers are also asked to remove coats and jackets, passing them through the baggage screening system. This has the effect of making it easier for checkpoint personnel to observe possible concealed objects, such as explosives, under their remaining clothes, which are now less bulky and thus less likely to obscure the presence of concealed items.

As such, at least one known airport screening system relies on manual observations to verify the identity of the passenger and also utilizes electronic scanners and metal detectors to ascertain whether the passenger or the luggage includes any weapons or explosives. Moreover, each passenger is subjected to the same level of screening without regard to the threat that may be posed by the passenger. As a result, the known system is time-consuming for the passengers, and does not alert the security personnel when a low threat passenger or high threat passenger is being screened such that the security personnel may either increase or decrease the level of screening that the passenger or the passenger's personal effects are subjected to.

BRIEF DESCRIPTION OF THE INVENTION

In one aspect, an inspection system is provided. The inspection system includes a first subsystem including a first identity verification system and a passenger screening system each configured to receive information from a passenger and store the verified information in a database, and a second subsystem including at least a second identity verification system configured to receive information from the passenger, the second subsystem configured to compare the verified identity information to the information received from the passenger at the second subsystem to verify the identity of the passenger.

In another aspect, an inspection system is provided. The inspection system includes a first kiosk including a first identity verification system and a passenger screening system each configured to receive information from a passenger and store the verified information in a database, a second kiosk positioned remotely from the first kiosk, the second kiosk including at least a second identity verification system configured to receive information from the passenger, the second kiosk configured to compare the verified identity information to the information received from the passenger at the second kiosk to verify the identity of the passenger, and a communications network coupled between the first and second kiosks.

In a further aspect, receiving at the first kiosk information including passenger identity information and passenger prescreening information, storing the information received at the first kiosk in a database, receiving at second kiosk information including the passenger identity information and the passenger prescreening information, comparing the information stored in the database with information received at the second kiosk to identity the passenger.

DETAILED DESCRIPTION OF THE INVENTION

Figure 1:
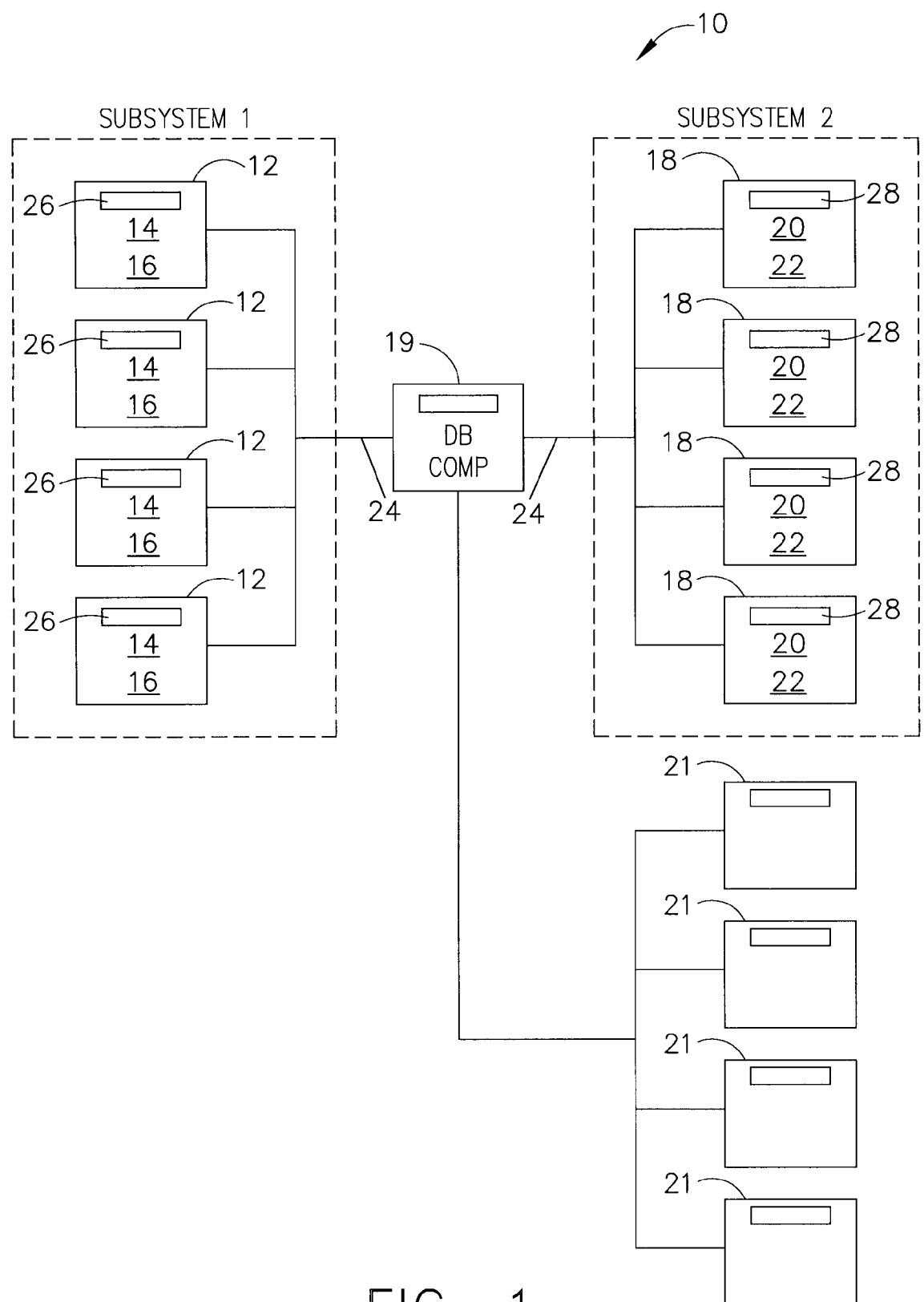
FIG. 1 is a simplified schematic illustration of an exemplary passenger identification and screening system 10.
Figure 2:
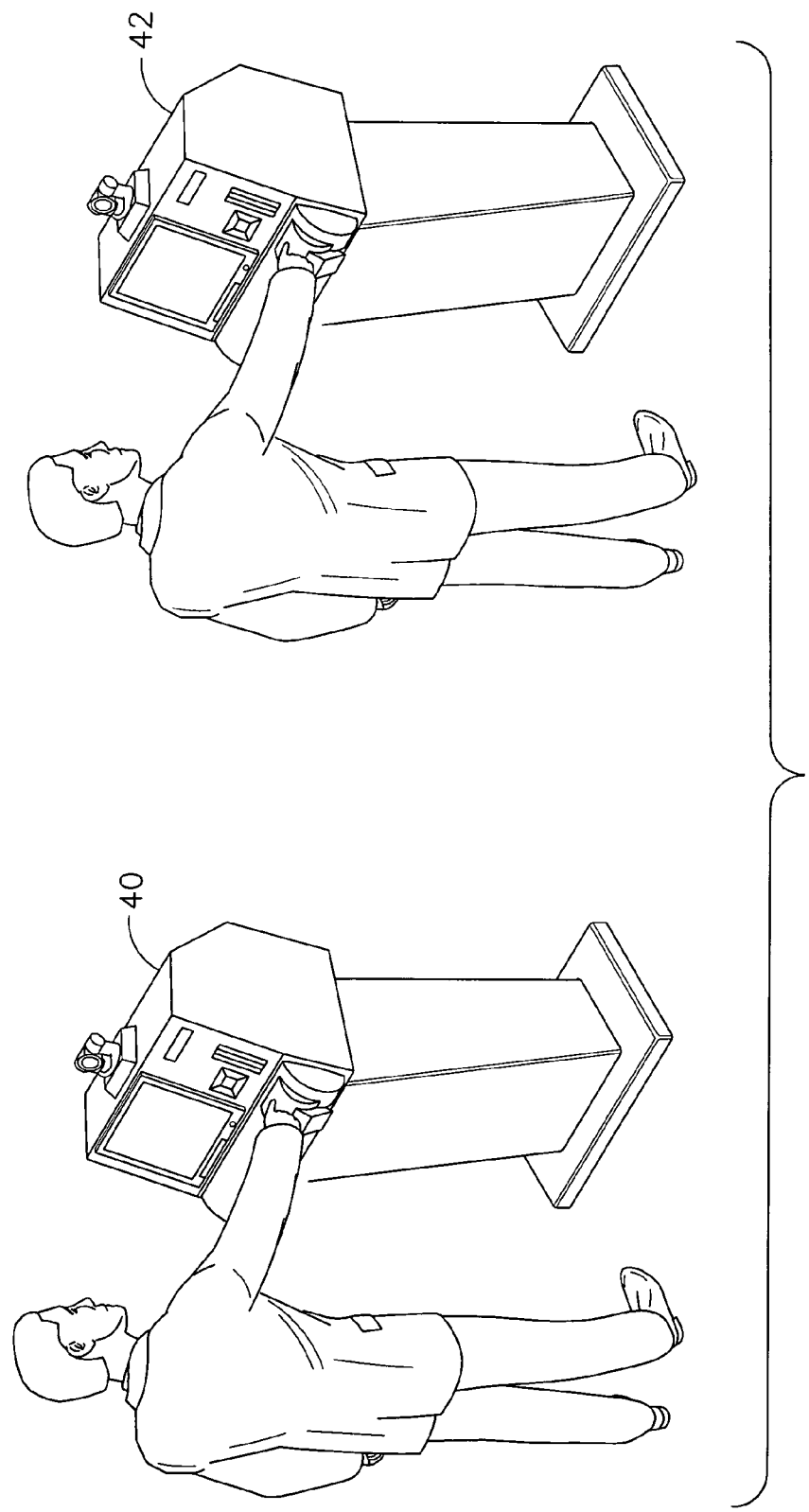
FIG. 2 is a perspective view of a portion of the passenger identification and screening system 10 shown in FIG. 1.
Figure 3:
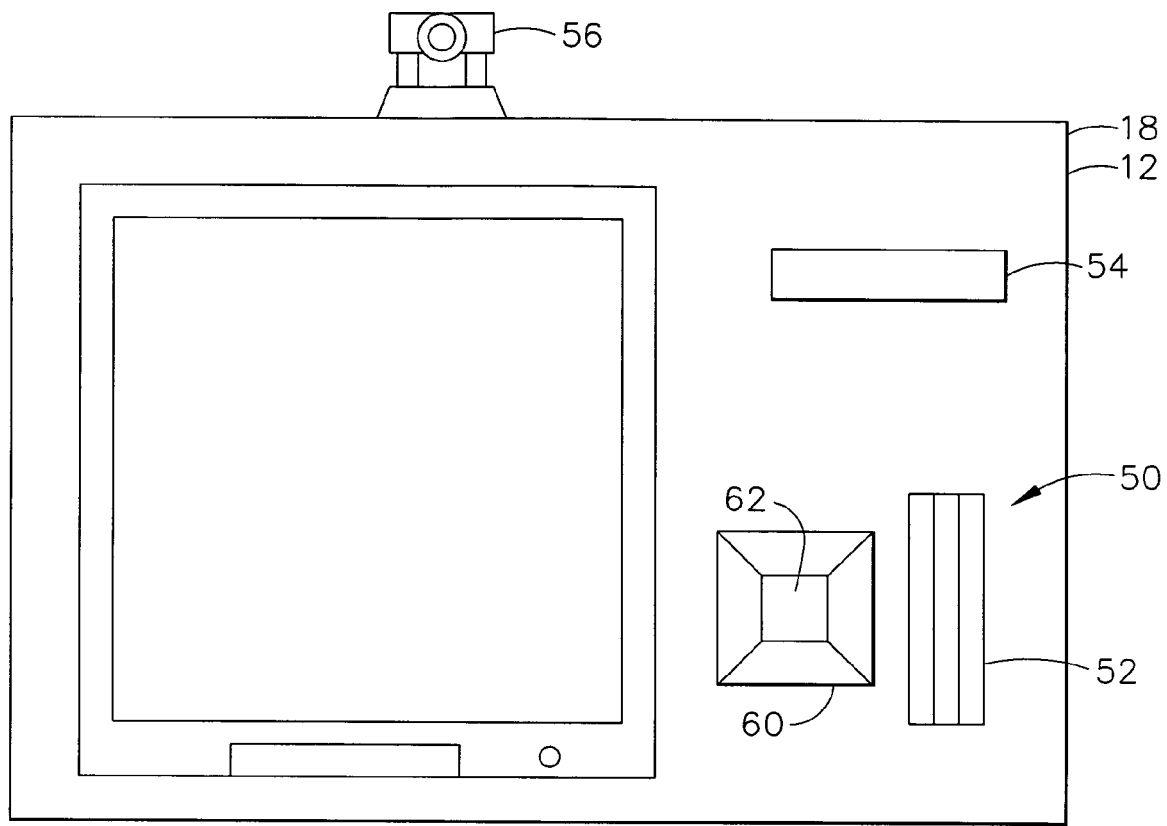
FIG. 3 is a front view of a portion of the kiosk shown in FIG. 2.

FIG. 1 is a simplified schematic illustration of an exemplary passenger identification and screening system 10. FIG. 2 is a perspective view of a portion of the passenger identification and screening system 10 shown in FIG. 1. FIG. 3 is a front view of a portion of the kiosk shown in FIG. 2. In the exemplary embodiment, system 10 includes a first subsystem 12 that includes at least a passenger verification system 14 and a passenger screening system 16, and a second subsystem 18 that includes at least a passenger verification system 20. In the exemplary embodiment, first subsystem 12 and second subsystem 18 are each installed in a standalone kiosk. Optionally, either first subsystem 12 and/or second subsystem 18 may be installed within a wall for example.

In the exemplary embodiment, system 10 includes a plurality of first subsystems 12 that are communicatively coupled to at least one subsystem 18, preferably a plurality of subsystems 18, via a communications bus 24 that is coupled between first and second subsystems 12 and 18. Each first and second subsystem 12 and 18 includes a computer 26 and 28 respectively, that enable a passenger or operator to input commands or receive biometric data from the operator and allow outputs generated by subsystems 12 and 18 to be delivered to a database computer 19 via communications bus 24. The information may then be utilized by other computer systems 21 for data analysis or utilized by an operator of any one of the computers within systems 21. In one embodiment, subsystems 12 and 18 are each hardwired to database computer 19. In another embodiment, subsystems 12 and 18 are each communicatively coupled to database computer 19 using a local area network or an internet connection.

As shown in FIG. 2, subsystem 12 is housed in a first kiosk 40 and subsystem 18 is housed within a second kiosk 42. In the exemplary embodiment, each respective kiosk 40 and 42 include a respective computer 26 and 28 that are each housed within kiosk 40 and 42, respectively. As such, kiosk 40 includes a passenger prescreening capability that will be discussed later herein. In the exemplary embodiment, kiosk 40 is positioned proximate to the location near the agent who validates a passenger's photo ID with the name on the boarding pass. This is sometimes at the entrance of the security queue or optionally at the exit of the security queue. Whereas, kiosk 42 is preferentially located at the divest area of the security lane, e.g. at the entrance to the metal detector and x-ray machine.

In the exemplary embodiment, passenger verification and/or tracking systems 14 and 20 may each be implemented utilizing a boarding pass scanner 50 that includes a bar code reader system 52 that is configured to read a bar code that is printed on each respective ticket presented by the operator or passenger. In another embodiment, passenger verification systems 14 and 20 may each be implemented utilizing a radio frequency identification device (RFID) that may be attached to or integrated with the boarding pass to enable the boarding pass scanner 50 to read the identification code stored within the RFID tag. During use, RFID tags receive and respond to radio frequency (RF) signals to provide information, for example, related to the boarding pass to which the RFID tag is attached. For example, modulators of the RFID tags may transmit back a signal using a transmitter or reflect back a signal to an RFID reader, i.e. boarding pass scanner 50. In another embodiment, at least one of passenger verification systems 14 and/or 20 may each be implemented utilizing a biometric means 56 such as, but not limited to, an iris scan device, a fingerprint scan device, a facial image recognition system, and/or a voice recognition system. In another embodiment, passenger verification systems 14 and 20 may each be implemented utilizing a card reader system 54 whereby passenger information may be encoded on a magnetic strip, optical read codes, an RF-read memory chip, or other embedded media onto the card. Optionally, kiosk 40 may include a printer that is configured to generate an identification ticket including the bar that is subsequently read by the second subsystem 18 housed within kiosk 42.

In the exemplary embodiment, passenger screening system 16 may be implemented utilizing a fingertip trace explosive detection system 60 that is capable of detecting minute particles of interest such as traces of narcotics, explosives, and other contraband on the passenger's finger or hand for example. In the exemplary embodiment, detection system 60 is located proximate to boarding pass scanner 50 such that as the passenger passes the boarding pass through scanner 50 at least a portion of the passenger's hand approximately simultaneously passes over detection system 60. Optionally, the passenger is prompted to press a button to activate detection system 60 such that trace materials on the finger surface are collected and then analyzed by detection system 60.

In the exemplary embodiment, trace explosive detection system 60 includes an ion trap mobility spectrometer 62 that is utilized to determine whether any substantially minute particles of interest such as traces of narcotics, explosives, and other contraband is found on the passenger's finger. For example, the ion trap mobility spectrometer 62 is preferentially useful in identifying trace explosives or other contraband on a passenger's finger that may be indicative of the passenger recently manipulating explosives or other contraband and as such does not require imaging or localization.

In the exemplary embodiment, all the data or information submitted by the passenger into the first subsystem 12 and or automatically collected by the first subsystem 12 is stored within a database, e.g. within database computer 19, that is accessible between subsystems 12 and 18 via communications link 24. For example, first subsystem 12 may combine the ticket/boarding pass information generated by passenger verification system 14 and the explosive detection results generated by passenger screening system 16 into a computer 26 housed within kiosk 40. The combined information is then transmitted to database computer 19 via communications link 24.

Second subsystem 18 is then utilized to retrieve the passenger data transmitted by first subsystem 12. More specifically, the information is retrieved when the passenger arrives at the security-screening lane via kiosk 42. In the exemplary embodiment, the first passenger verification and/or tracking systems means utilized by the passenger to self-initiate at first kiosk 40 is also utilized by kiosk 42 to verify the information. For example, if the passenger utilizes boarding pass scanner 50 to verify his identity, second subsystem 18 includes a comparable boarding pass scanner to re-verify the identity of the passenger at the second kiosk 42. Optionally, if the passenger's identity was verified using other means, for example, the iris scan, facial image recognition system, hand scan, voice scan, etc., then second kiosk 42 includes similar means to reverify the identity of the passenger.

Once the identity of the passenger has be reverified by second subsystem 18, second subsystem 18 utilizes the results from the passenger screening system 16 sent from the first subsystem 12 to select an appropriate passenger screening level for the passenger at the security screening lane. For example, if the results obtained by fingertip trace explosive detection system 60 in the first subsystem 12 is negative, security personnel may choose to have the passenger traverse a metal detector prior to boarding the aircraft for example. However, if the results obtained by fingertip trace explosive detection system 60 in the first subsystem 12 is positive, security personnel may opt to perform a more thorough inspection of the passenger prior to the passenger boarding the aircraft. For example, security personnel may choose to have the passenger remove his shoes and other clothing such as coats and subject these articles to a quadrupole resonance (QR) detection system. Moreover, security personnel may choose to pat down or utilize a metal detecting wand on the passenger to ensure that the passenger is not concealing any explosives or other contraband. As a result, the first subsystem 12 is utilized to perform passenger verification and also to perform an initial or pre-screening on the passenger. The second subsystem 18 then utilizes the information from the first subsystem 12 to reverify the identity of the passenger and also to alert security personnel when a passenger may require further security screening.

The combined subsystems allow a passenger to self-initiate themselves to the computerized database with the explosives screening process and then have this information automatically recalled by the full security process when the passenger arrives at the security-screening lane. This configuration also allows passengers that have recently had their identity verified by a security agent to undergo a pre-screen for explosives. The screening result would be used to dynamically adjust the security level of the screening lane as necessary, allowing the overall system 10 to covertly place higher security emphasis on the appropriate passengers and thus allows a higher level of security with minimal passenger inconvenience, traffic flow restrictions and agent resource usage.

While the invention has been described in terms of various specific embodiments, those skilled in the art will recognize that the invention can be practiced with modification within the spirit and scope of the claims.

What is claimed is:

1. An inspection system, comprising:
    a first subsystem comprising a first automated identity verification system a passenger screening system, and a detection system, said first automated identity verification system configured to receive a first identification of a passenger and store the first identification in a database, said passenger screening system configured to directly detect information from the passenger and store the detected information in the database, and said detection system configured to prescreen the passenger for explosives and store prescreening information in said database; and
    a second subsystem comprising at least a second automated identity verification system configured to receive a second identification of the passenger, verify an identity of the passenger by comparing the first identification to the second identification, receive the prescreening information, and adjust a level of passenger follow-up screening based on the prescreening information.

2. An inspection system in accordance with claim 1 wherein said detection system comprises a fingertip trace explosive detection system.

3. An inspection system in accordance with claim 2 wherein said fingertip trace explosive detection system comprises an ion trap mobility spectrometer.

4. An inspection system in accordance with claim 1 wherein said first automated identity verification system and said second automated identity verification system each comprises a boarding pass scanner.

5. An inspection system in accordance with claim 4 wherein said boarding pass scanner includes a bar code reader system that is configured to read a bar code printed on a boarding pass.

6. An inspection system in accordance with claim 4 wherein said boarding pass scanner includes an RFID tag reader that is configured to receive a signal from an RFID tag coupled to said boarding pass.

7. An inspection system in accordance with claim 1 wherein said first automated identity verification system and said second automated identity verification system each comprises biometric means to identify the passenger.

8. An inspection system in accordance with claim 7 wherein said biometric means comprises at least one of an iris scanner, a hand scanner, a voice recognition system, and a facial recognition system.

9. An inspection system in accordance with claim 1 wherein said first subsystem is located remotely from said second subsystem, said inspection system further comprising a communications network coupled between said first and second subsystems.

10. An inspection system in accordance with claim 1 wherein said first automated identity verification system comprises a card reader configured to receive passenger inputted identity information from the passenger that is stored on at least one of a magnetic strip, an optical read code, and an RF-read memory chip, and said second automated identity verification system is configured to compare the inputted identity information entered into said card reader with the information received from the passenger utilizing the second subsystem to facilitate verifying the identity of a passenger.

11. An inspection system comprising:
    a first kiosk comprising a first automated identity verification system a passenger screening system, and a detection system, said first automated identity verification system configured to receive a first identification of a passenger and store the first identification in a database, said passenger screening system configured to directly detect information from the passenger and store the detected information in the database, and said detection system configured to prescreen the passenger for explosives and store prescreening information in said database;
    a second kiosk positioned remotely from said first kiosk, said second kiosk comprising at least a second automated identity verification system configured to receive a second identification of the passenger, verify an identity of the passenger by comparing the first identification to the second identification, receive the prescreening information, and adjust a level of passenger follow-up screening based on the prescreening information; and
    a communications network coupled between said first and second kiosks.

12. An inspection system in accordance with claim 11 wherein said detection system comprises a fingertip trace explosive detection system.

13. An inspection system in accordance with claim 12 wherein said fingertip trace explosive detection system comprises an ion trap mobility spectrometer.

14. An inspection system in accordance with claim 11 wherein said first automated identity verification system and said second automated identity verification system each comprises a boarding pass scanner.

15. An inspection system in accordance with claim 14 wherein said boarding pass scanner includes a bar code reader system that is configured to read a bar code printed on a boarding pass.

16. An inspection system in accordance with claim 14 wherein said boarding pass scanner includes an RFID tag reader that is configured to receive a signal from an RFID tag coupled to said boarding pass.

17. An inspection system in accordance with claim 11 wherein said first automated identity verification system and said second automated identity verification system each comprises biometric means to identify the passenger.

18. An inspection system in accordance with claim 17 wherein said biometric means comprises at least one of an iris scanner, a hand scanner, a voice recognition system, and a facial recognition system.

19. An inspection system in accordance with claim 11 wherein said first kiosk is located proximate an airport boarding pass and identification validation station and said second kiosk is positioned proximate an airport security screening lane.

20. An inspection system in accordance with claim 11 wherein said first automated identity verification system comprises a card reader configured to receive passenger inputted identity information from the passenger that is stored on at least one of a magnetic strip, an optical read code, and an RF-read memory chip, and said second automated identity verification system is configured to compare the inputted identity information entered into said card reader with the information received from the passenger utilizing the second subsystem to facilitate verifying the identity of a passenger.

21. A method for inspecting a subject utilizing an inspection system that includes at least a first kiosk, a second kiosk positioned remotely from the first kiosk, and a communications network coupled between the first kiosk and the second kiosk, said method comprising:

receiving from the subject, at the first kiosk, information including first passenger identity information and passenger prescreening information, the passenger pre-screening information including contraband detection results;

storing the information received at the first kiosk in a database;

receiving at the second kiosk information including second passenger identity information and the passenger pre-screening information, the second passenger identity information received at the second kiosk from the subject; and comparing the first passenger identity information stored in the database with the second passenger identity information received at the second kiosk to verify an identity of the subject.

22. A method in accordance with claim 21 further comprising selecting a level of follow-up passenger screening utilizing the information stored in the database.

23. A method in accordance with claim 21 wherein receiving at the first kiosk information including passenger identity information further comprises receiving fingertip trace explosive information at the first kiosk and storing the fingertip trace explosive information in the database.

24. A method in accordance with claim 21 wherein receiving at the first kiosk information including passenger pre-screening information further comprises receiving passenger boarding pass information at the first kiosk and storing the passenger boarding pass information in the database.

25. A method in accordance with claim 21 further comprising:

retrieving the passenger identity information and the passenger pre-screening information from the database utilizing the second kiosk; and adjusting a level of passenger follow-up screening based on the retrieved information.

* * * * *